(12) United States Patent
Zhao et al.

(10) Patent No.: US 8,236,784 B2
(45) Date of Patent: Aug. 7, 2012

(54) COMPOSITION COMPRISING THREITOL PHOSPHATE AND SALTS THEREOF

(75) Inventors: Hui Zhao, Santa Paula, CA (US); Krzysztof Bojanowski, Santa Paula, CA (US); Fariba Aria, Cupertino, CA (US); Reza Mortezaei, Cupertino, CA (US)

(73) Assignee: Sunny Biodiscovery, Inc., Santa Paula, CA (US)

( * ) Notice: Subject to any disclaimer, the term of this patent is extended or adjusted under 35 U.S.C. 154(b) by 267 days.

(21) Appl. No.: 12/620,138

(22) Filed: Nov. 17, 2009

(65) Prior Publication Data

US 2010/0291185 A1 Nov. 18, 2010

Related U.S. Application Data

(63) Continuation of application No. PCT/US2008/063634, filed on May 15, 2008.

(60) Provisional application No. 60/930,573, filed on May 17, 2007.

(51) Int. Cl.
| | |
|---|---|
| *A61K 31/66* | (2006.01) |
| *A61K 31/6615* | (2006.01) |
| *A61K 8/55* | (2006.01) |
| *C07F 9/09* | (2006.01) |
| *A61P 17/00* | (2006.01) |
| *A61P 19/00* | (2006.01) |
| *A61Q 11/00* | (2006.01) |
| *A61Q 19/00* | (2006.01) |
| *A61Q 19/08* | (2006.01) |

(52) U.S. Cl. .......... 514/103; 514/106; 514/129; 424/59; 424/62

(58) Field of Classification Search ................ None
See application file for complete search history.

(56) References Cited

FOREIGN PATENT DOCUMENTS

| WO | 93/23054 A | 11/1993 |
| WO | 97/05883 A | 2/1997 |

OTHER PUBLICATIONS

Berge et al. Pharmaceutical Salts. Journal of Pharmaceutical Sciences (Jan. 1977) vol. 66, No. 1, pp. 1-19.*
Walker et al., J. Org. Chem., 70:9955-9959 (2005). XP002489153.
Databsse CA [Online] Chemical Abstracts Service, Columbus, Ohio, US; Miwa, Shigeru: "Substance microdetermination in body fluids based on cyclic enzyme reactions" XP002489154 retrieved from STN Database accession No. 1989:530268.

* cited by examiner

*Primary Examiner* — David J Blanchard
*Assistant Examiner* — Peter Anthopolos
(74) *Attorney, Agent, or Firm* — Nixon Peabody LLP

(57) ABSTRACT

This application discloses compositions containing synthetic threitol phosphates, in particular threitol monophosphate, threitol-bis-phosphate, threitol diphosphate, and/or threitol triphosphate. The threitol phosphates are useful in treating wounds, for cosmetic applications, and for bone and periodontal regeneration.

4 Claims, 4 Drawing Sheets

COMPOSITION COMPRISING THREITOL PHOSPHATE AND SALTS THEREOF

CROSS REFERENCE TO RELATED APPLICATIONS

This application claims benefit under 35 U.S.C. §120 and is a continuation of International PCT Application No. PCT/US2008/063634, filed May 15, 2008, which claims the benefit under 35 U.S.C. §119(e) to U.S. Provisional Application Ser. No. 60/930,573, filed May 17, 2007. The contents of both applications are incorporated by reference herein in their entirety.

BACKGROUND OF THE INVENTION

Aging, damaged and wounded skin presents symptoms, which could benefit from the stimulation of angiogenesis (the growth or assembly or formation of blood vessels), fibroblast growth and extracellular matrix deposition, such as type I collagen and hyaluronic acid. The stimulation of the above is also beneficial for periodontal regeneration, with angiogenesis and osteoblast proliferation often required for bone regeneration.

Basic fibroblast growth factors and chemical compounds such as magnesium ascorbyl phosphate have been used to assist in cell growth and regeneration. However, it is desirable to have additional compounds that can either be used alone or in conjunction with the known treatments. This invention answers that need.

SUMMARY OF THE INVENTION

This invention relates to a composition comprising at least one threitol phosphate selected from the group consisting of threitol monophosphate, threitol-bis-phosphate, threitol diphosphate, threitol triphosphate, and salts thereof.

The invention also relates to a method of improving the skin appearance, skin integrity, or skin health. In one embodiment, the method involves contacting the skin with a therapeutically effective amount of a composition comprising threitol phosphates. In another embodiment, the method involves administering to a patient in need thereof a pharmaceutically effective amount of a formulation comprising threitol phosphates.

The invention also relates to a method of treating a wound. The method involves contacting the wound with a therapeutically effective amount of a composition comprising threitol phosphates.

The invention also relates to a method of improving bone and periodontal regeneration. The method involves administering to the bone or periodontal area in need thereof an effective amount of a composition comprising threitol phosphates.

BRIEF DESCRIPTIONS OF THE FIGURES

FIG. 1 is a scheme depicting the synthesis of threitol-1 tri, di, and monophosphate.

FIG. 2 shows a chart depicting the effect of sSBD.4 on the proliferation of human dermal fibroblasts (HDF) and on the type I collagen in the medium conditioned by these cells. FIG. 2A depicts sSBD.4 stimulating the proliferation of HDF. FIG. 2B depicts sSBD.4 increasing type I collagen levels in the HDF-conditioned medium.

DETAILED DESCRIPTION OF THE INVENTION

This invention is directed to the synthesis and new use of the family of phosphates of threitol, and the salts and derivatives thereof. In particular, the phosphates of threitol comprise at least one of the following phosphates: threitol monophosphate, threitol-bis-phosphate, threitol diphosphate, threitol triphosphate, or a salt or derivative thereof. Threitol diphosphate, or a salt thereof, is the preferred threitol phosphate. Any salt or derivates known to those of skill in the art is included within this definition. Calcium salts and sodium salts are the preferred salts.

In this application, the threitol phosphates are collectively referred to as "sSBD.4." A reference to sSBD.4 means that at least one of the four synthetically produced threitol phosphates (or salts or derivatives thereof) is present in the composition. Often times, sSBD.4 will be a mixture that contains threitol monophosphate, threitol diphosphate, and threitol triphosphate. In a preferred embodiment, the majority of the mixture is threitol diphosphate.

sSBD.4 may be used to stimulate endothelial, fibroblast, keratinocyte, and osteoblast cell proliferation, as well as extracellular matrix components, such as, but not limited to collagens and hyaluronic acid. This type of stimulation results in improvements in wound healing, bone and periodontal regeneration, as well as in the general improvement of skin appearance and its overall health.

Thus, the composition containing sSBD.4 can represent a variety of products useful for such treatments. For example, the composition can be an edible food product, a cosmetic composition, or a bone or non-invasive periodontal treatment, each discussed below. The composition containing sSBD.4 can also be a pharmaceutical composition that contains sSBD.4, a pharmaceutically acceptable excipient, and other components known to those of skill in the art commonly found in pharmaceutical compositions.

Figure 1:
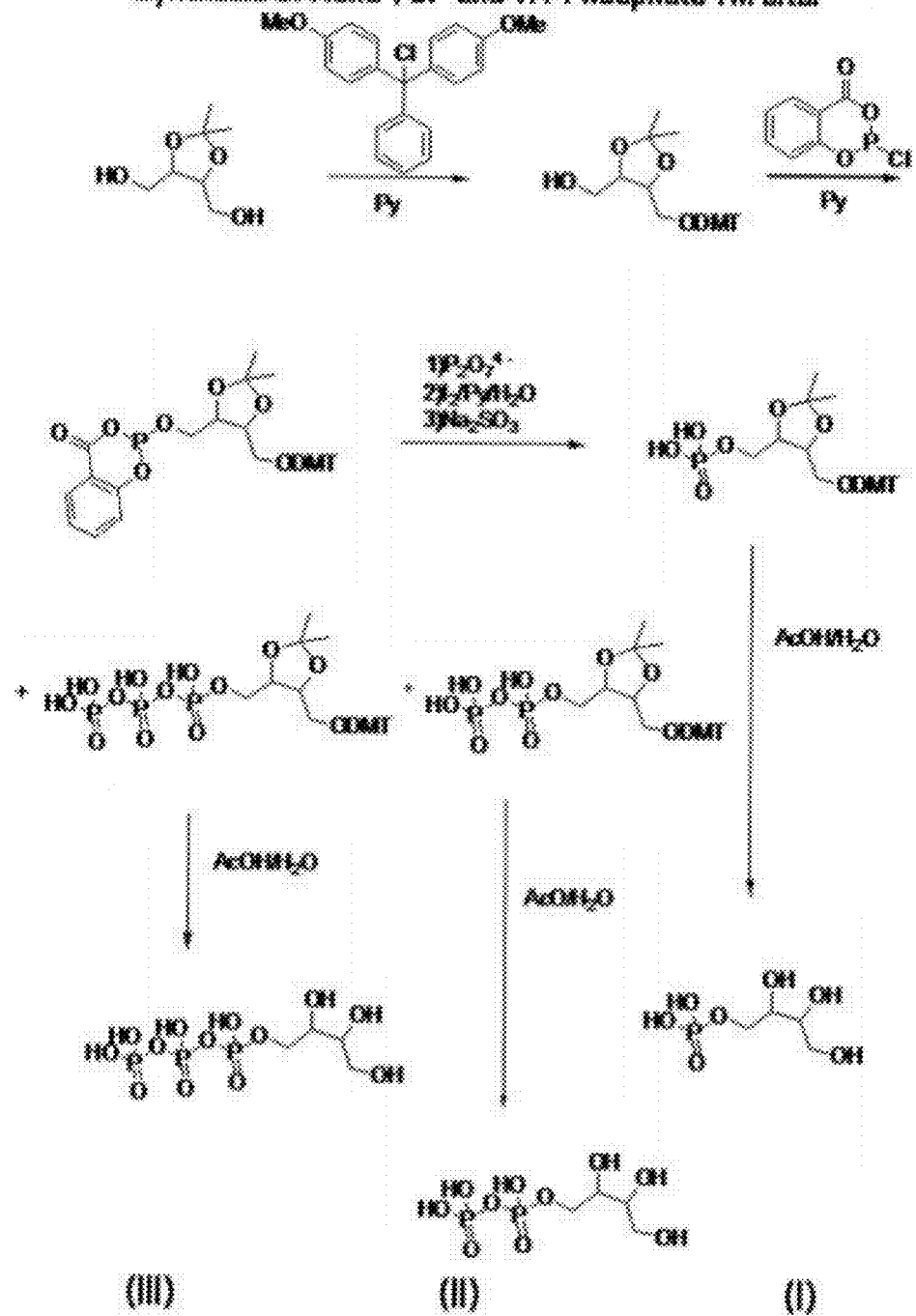

Threitol phosphates may be prepared in accordance with the reaction scheme shown in FIG. 1. This mixture may then be further isolated to achieve individual threitol phosphate compounds using techniques known in the art. Alternatively, threitol phosphates can be synthesized based on the published method by Tayeb et al., J. Med. Chem. 2006, 49, 7076-7087, herein incorporated by reference in its entirety, where the pyrimidine is replaced with 2,3-O-Isopropylidene-D-Threitol. This alternative method allows for the production of individual threitol phosphate compounds.

Threitol phosphates are believed to be present in the herb *Angelica sinensis*. However, the exact structure of the threitol phosphates is, at this point, unclear. If present in *Angelica sinensis*, threitol phosphates exist as a multi-component extract containing many other ingredients, including proteins and various other components of the *Angelica sinensis* root.

Therefore, an embodiment of this invention relates to a composition comprising at least one purified threitol phosphate selected from the group consisting of threitol monophosphate, threitol-bis-phosphate, threitol diphosphate, threitol triphosphate, their salts, and mixtures thereof. In a preferred embodiment, the purified threitol phosphates are substantially free of naturally occurring *Angelica sinensis*, proteins and similar components. The threitol phosphates preferably have a purity of at least 95%, more preferably, at least 99%. As such, another embodiment of this invention relates to a composition consisting essentially of at least one threitol phosphate selected from the group consisting of threitol monophosphate, threitol-bis-phosphate, threitol diphosphate, threitol triphosphate, their salts, and mixtures thereof.

Pharmaceutical Applications

The present invention provides a pharmaceutically acceptable formulation comprising sSBD.4, useful in the methods of the present invention. In one embodiment, the invention is directed to a method of improving the skin appearance, skin integrity, or skin health of a patient, comprising administering to a patient in need thereof a pharmaceutically effective amount of a formulation comprising at least one threitol phosphate selected from the group consisting of threitol monophosphate, threitol-bis-phosphate, threitol diphosphate, threitol triphosphate, and salts and derivatives thereof. The formulation may be in the form of a tablet, pill, injectable, slow-release matrix, or other known means of administering a pharmaceutical formulation. The formulation may be crystalline in nature, which enables sSBD.4 to be packaged in a sachet that is decanted into a potable liquid for oral administration to the patient. In this embodiment, the liquid can be a syrup or, more conveniently, a commonly consumed liquid, such as water, fruit juice, or cola. When desirable, the liquid can be glucose-free.

A decided practical advantage of the compounds of the present invention is that the compounds can be administered in any convenient manner such as by the oral, intravenous, intramuscular, topical, intraperitoneal, periodontal or subcutaneous routes. sSBD.4 can be orally administered, for example, with an inert diluent or with an assimilable edible carrier, or it can be enclosed in hard or soft shell gelatin capsules, or compressed into tablets, or incorporated directly with the food of the diet. For oral therapeutic administration, the agent extracts can be incorporated with excipients and used in the form of ingestible tablets, buccal tablets, troches, capsules, elixirs, suspensions, syrups, wafers, and the like. Such compositions and preparations should contain enough of the sSBD.4 to deliver a therapeutically effective amount.

The tablets, troches, pills, capsules, and the like may also contain any of the following: a binder such as gum tragacanth, acacia, corn starch, or gelatin; excipients such as dicalcium phosphate; a disintegrating agent such as corn starch, potato starch, alginic acid, and the like; a lubricant such as magnesium stearate; a sweetening agent such as saccharin; and/or a flavoring agent such as peppermint, oil of wintergreen, or cherry flavoring. When the dosage unit form is a capsule, it can contain, in addition to materials of the above types, a liquid carrier. Various other materials can be present as coatings or to otherwise modify the physical form of the dosage unit. For instance, tablets, pills, or capsules can be coated with shellac. A syrup or elixir can contain the active compound, a sweetening agent, methyl and propylparabens as preservatives, and a flavoring such as cherry or orange flavor. Of course, any material used in preparing any dosage unit form should be pharmaceutically pure and substantially non-toxic in the amounts employed. In addition, sSBD.4 can be incorporated into sustained-release preparations and formulations. sSBD.4 can also be administered parenterally or intraperitoneally. A solution of the active compound as a free acid or pharmacologically acceptable salt can be prepared in water suitably mixed with a surfactant and slow release matrices, such as hydroxypropylcellulose, polyethylene glycol or polylactide-glycolide and its derivatives and combinations with polytetrafluoroethylene. Dispersions can also be prepared in glycerol, liquid polyethylene glycols and mixtures thereof, and in oils. Under ordinary conditions of storage and use, these preparations contain a preservative to prevent the growth of microorganisms.

The pharmaceutical forms suitable for injectable use include sterile aqueous solutions, the aforementioned slow release matrices, or dispersions and sterile powders for the extemporaneous preparation of sterile injectable solutions or dispersions. When desirable, the form should be sterile and, in final form, fluid to the extent that easy syringability exists.

The pharmaceutical forms suitable for topical use include oil and water emulsions and liposomal formulations and other slow release matrices, as well as lotions, creams, and ointments commonly used for topical administration of drugs.

The carrier can be a solvent or dispersion medium containing, for example, water, ethanol, polyol, for example, glycerol, propylene glycol, and liquid polyethylene glycol, and the like, suitable mixtures thereof, and vegetable oils. The proper fluidity can be maintained, for example, by the use of a coating such as lecithin, by the maintenance of the required particle size in the case of dispersion and by the use of surfactants. The prevention of the action of microorganisms can be brought about by various anti-bacterial and anti-fungal agents, for example, parabens, chlorobutanol, phenol, sorbic acid, thimerosal, and the like. In many cases, it will be preferable to include isotonic agents, for example sodium chloride. Prolonged absorption of the injectable compositions can be brought about by the use in the compositions of agents delaying absorption, for example, aluminum monostearate and gelatin.

Sterile injectable solutions can be prepared by incorporating the sSBD.4 in the required amount in the appropriate solvent with various other ingredients enumerated above, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique, which yield a powder of the active ingredient plus any additional desired ingredient from previously sterile filtered solution thereof.

A pharmaceutically acceptable carrier typically includes any and all solvents, dispersion media, coatings, antibacterial and antifungal agents, isotonic agents, absorption delaying agents, slow-release matrices, and the like. The use of such media and agents for pharmaceutical active substances is well known in the art. Except insofar as any conventional media or agent is incompatible with the active ingredient, its use in the therapeutic compositions of the invention is contemplated. Supplementary active ingredients and slow release vehicles can be incorporated into the compositions of the invention.

It is advantageous to formulate parental and other compositions in dosage unit form for ease of administration and uniformity of dosage. Dosage unit form as used herein refers to physically discrete units suited as unitary dosages for the subjects to be treated; each unit containing a predetermined quantity of sSBD.4 calculated to produce the desired therapeutic effect in association with the pharmaceutical carrier.

Alternatively, the skin can be treated by applying the sSBD.4-containing composition directly to the skin. This embodiment of the invention relates to a method of improving the skin appearance, skin integrity, or skin health, comprising contacting the skin with a therapeutically effective amount of a composition comprising at least one threitol phosphate selected from the group consisting of threitol monophosphate, threitol-bis-phosphate, threitol diphosphate, threitol triphosphate, and salts and derivatives thereof.

Typically, the skin is aged, photoaged, wounded, or otherwise damaged. An embodiment of this invention is directed towards treating wounded skin where the wounded skin contains an ulcer. The ulcer may be a skin ulcer and/or a chronic ulcer.

The composition can be contacted with the skin through any means known in the art, for instance in an aqueous soaking solution. The skin can be further contacted with collagen or cotton fibers, foams, metalloproteinase-binding cotton fibers, polysaccharides, skin substitutes, antibiotics, antimicrobial agents, or a combination thereof.

The composition—either as a pharmaceutical formulation or therapeutic composition—can contain a growth factor. Suitable growth factors include fibroblast growth factors (FGF), such as FGF-1, FGF-2, and FGF-4; tymosins; platelet-derived growth factors (PDGF); insulin-like growth factors (IGF), such as IGF-1 and IGF-2; epidermal growth factors (EGF); transforming growth factors (TGF), such as TGF-α and TGF-β; cartilage-inducing factors, such as factor-A and -B; osteoid-inducing factors; bone growth factors, such as osteogenin; collagen-growth factors, bone morphogenic proteins; and heparin-binding growth factors, such as factors-1 and -2. The biologically active derivatives of the above-listed growth factors may also be used, as well as antiseptics of the compositions.

Another aspect of the invention includes promoting angiogenesis in tissue by directly contacting the tissue with the sSBD.4-containing composition in an amount effective to promote angiogenesis in the tissue. The tissue can be fibrous, skin, endothelial, vesicular, cardiac, cerebrovascular, muscular, vascular, transplanted, or wounded. The tissue can also be ischemic wherein the ischemic tissue is aged or photoaged skin, myocardial ischemic tissue, cerebrovascular ischemic tissue, or veno-occlusive diseased tissue. A further embodiment of the present invention is the promotion of angiogenesis by sSBD.4 in the myocardial ischemic tissue wherein the myocardial ischemic tissue is coronary artery disease.

The stimulation of angiogenesis and fibroblast growth by sSBD.4 may be a valuable treatment for other cardiovascular diseases, stroke, peptic ulcers, wounds, personal care (such as skin, lip, hair care), and for other conditions where the stimulation of fibroblast growth, metabolic activity, extracellular matrix components, and angiogenesis, or protection of vascular networks is beneficial.

In another embodiment, the invention is directed to methods of use of sSBD.4 in treatment of diseases or conditions which would benefit from endothelial, fibroblast, keratinocyte, and/or osteoblast cell proliferation, including, but not limited to treatment of aged, photoaged or damaged skin, cutaneous wounds, chronic ulcers, e.g., skin ulcers, periodontal lesion healing and bone regeneration.

Wound-Healing Applications

The present invention provides improved methods for promoting wound healing and reducing scar formation. One embodiment of the invention relates to a method of treating a wound, comprising contacting the wound with a therapeutically effective amount of a composition comprising at least one threitol phosphate selected from the group consisting of threitol monophosphate, threitol-bis-phosphate, threitol diphosphate, threitol triphosphate, and salts and derivatives thereof.

As used herein, the term "wound" is used throughout the specification to describe skin wounds, which are treated by the formulations and the methods, described herein as well as tissue wounds. A skin wound is defined herein as a break in the continuity of skin tissue that is caused by direct injury to the skin. Several classes including punctures, incisions, excisions, lacerations, abrasions, atrophic skin, or necrotic wounds and burns generally characterize skin wounds. The compositions and methods of the invention are useful for enhancing the healing of all wounds of the skin. In particular, the present invention provides methods and compositions suitable for treatment of wounds in diabetics, normal patients and surgical patients.

A "tissue wound" as used herein is a wound to an internal organ, such as a blood vessel, intestine, colon, etc. The materials of the invention are useful for enhancing the wound healing process in tissue wounds whether they arise naturally or as the result of surgery. For instance, during the repair of arteries the vessel needs to be sealed and wound healing must be promoted as quickly as possible. The compositions of the invention can speed up that process. The compositions of the invention are also particularly useful for the treatment of damaged tissue in the colon.

The methods of the invention are also useful for preventing scar formation. The compositions can be used to prevent the formation of a scar at the same time as promoting wound healing. Alternatively, the compositions may be used for preventing scar formation by reducing or initiating regression of existing scars. Scar tissue as used herein refers to the fiber rich formations arising from the union of opposing surfaces of a wound.

The compositions and methods of the invention may also include additional therapeutic and/or pharmacologically acceptable agents. For instance, the compositions or methods may involve other agents for the treatment of wounds such as, for instance, dexpanthenol, collagens, alginates, skin substitutes, growth factors, enzymes or hormones, povidon-iodide, fatty acids, such as cetyl pyridinium chloride, antibiotics, metalloproteinase-binding cotton fibers, other wound dressings, and analgesics. Suitable growth factors include those listed above.

The sSBD.4-containing composition can be applied to the wound in various different manners. The composition may be applied to a dressing material, for example a dressing material that additionally contains collagen and/or alginate. Suitable dressing materials include adhesive medical tapes, bandages, and other dressing materials known in the art. The dressing material can be a porous material, a non-porous material, or a micro-porous material.

Alternatively, the sSBD.4-containing composition may be in the form of a gel, for instance, a gel that contains a gel-forming amount of a water-soluble or water-swellable pharmaceutically acceptable polymer, and one or more pharmaceutically acceptable excipient. Gels are often advantageous because of their ability to be hydrated and dehydrated. When desirable, the gel can be dehydrated to a preparation in the form of a foam or a powder form of the gel material. When used in conjunction with a dressing, the preparation can be attached or applied to a dressing, and the dressing then applied to the wound. Preferably, the foam or powder preparation is in a suitable form so that it will adhere to a wound for at least 24 hours and, during that time, enhance healing of the wound and help prevent infection of the wound. The preparation can be partially or fully rehydrated to form a hydro-gel prior to applying the dressing to the wound.

Cosmetic Applications

The sSBD.4-containing composition of the present invention may be utilized in the formulation of cosmetic compositions because of its novel properties in not only protecting and enhancing microcirculation, dermal fibroblast and keratinocyte growth, but also stimulating collagen I and other extracellular matrix component levels in the skin.

Cosmetic compositions are preparations applied to the surface of the body for the purpose of enhancing its appearance. These compositions can be make-up preparations, applied to bring about temporary effects, lasting only so long as the preparations remain on or in the skin, or treatment preparations, which effect no immediately noticeable change but which, after repeated use, are expected to have a beautifying effect.

The cosmetic compositions of the present invention may be skin care products such as lotions, creams, cleansers, gels, shampoos, conditioners, etc. Depending on the type of cosmetic, the cosmetic composition can contain other components typically found in the desired cosmetic, such as a UV-screening agent, whitening agents, or skin-soothing agents, such as dimethicone, allantoin or other FDA-approved skin-soothing agents. The compositions of the invention may be emulsions of liquid or semi-liquid consistency of the milk type, obtained by dispersion of an oil phase in an aqueous phase or vice versa; or suspensions or emulsions of soft consistency of the cream type; or slow-release matrices.

All oils used in the production of cosmetic compositions are suited for use in the compositions of the present invention. There may be mentioned hydrocarbons such as mineral oils, petrolatum and squalane; animal and vegetable triglycerides such as almond oil, peanut oil, wheat germ oil, linseed oil, jojoba oil, oil of apricot pits, oil of walnuts, oil of palm nuts, oil of pistachio nuts, oil of sesame seeds, oil of rapeseed, cade oil, corn oil, peach pit oil, poppyseed oil, pine oil, castor oil, soybean oil, avocado oil, safflower oil, coconut oil, hazelnut oil, olive oil, grapeseed oil, and sunflower seed oil; hydroxy-substituted $C_8$-$C_{50}$ unsaturated fatty acids and esters thereof; $C_1$-$C_{24}$ esters of $C_8$-$C_{30}$ saturated fatty acids such as isopropyl myristate, cetyl palmitate and octyldodecylmyristate (Wickenol 142); beeswax; saturated and unsaturated fatty alcohols such as behenyl alcohol and cetyl alcohol; fatty sorbitan esters; lanolin and lanolin derivatives; $C_1$-$C_{24}$ esters of dimer and trimer acids such as diisopropyl dimerate, diisostearylmalate, diisostearyldimerate and triisostearyltrimerate; and silicones such as water-insoluble silicones inclusive of non-volatile polyalkyl and polyaryl siloxane gums and fluids, volatile cyclic and linear polyalkylsiloxanes, polyalkoxylated silicones, amino and quaternary ammonium modified silicones, rigid cross-linked and reinforced silicones and mixtures thereof. All oils mentioned above can be also used together with this invention in liposomal, amphoteric or micellar formulations.

It is possible to use standard antioxidants such as t-butyl hydroquinone, butylated hydroxytoluene, α-tocopherol ascorbic acid, ferulic acid, lipoic acid and their derivatives and salts in the cosmetic compositions of the present invention, preferably, in amounts less than would normally be utilized.

Similarly, it is possible to use standard preservatives such as methyl, ethyl, propyl, butyl and isobutyl p-hydroxybenzoate (parabems), 2-phenoxyethanol, sorbic acid, ascorbic acid, ferulic acid, potassium sorbate, hexamidine diisothionate, imidazolidinylurea (Germall 115) or preservatives marketed under the names Kathon and Tridssan.

A wide variety of optional ingredients such as non-occlusive moisturizers, humectants, gelling agents, neutralizing agents, perfumes, coloring agents and surfactants can be added to the presently contemplated cosmetic compositions.

A humectant may be present in an amount of from about 0.1% to about 20%, preferably from about 1% to about 10% and especially from about 2% to about 5% by weight of the total composition. Suitable humectants include sorbitol, propylene glycol, butylene glycol, hexylene glycol, ethoxylated glucose derivatives, hexanetriol, glycerine, water-soluble polyglycerylmethacrylate lubricants (e.g., compositions available under the trademark Lubrajel) and panthenols (e.g. D-panthenol).

A hydrophilic gelling agent may be present in an amount of from about 0.01% to about 10%, preferably from about 0.02% to about 2% and especially from about 0.02% to about 0.5% by weight of the total composition. Suitable hydrophilic gelling agents include cellulose ethers (e.g., hydroxyethyl cellulose, hydroxypropylmethyl cellulose), polyvinylalcohol, guar gum, hydroxypropyl guar gum and xantham gum, as well as the acrylic acid/ethyl acrylate copolymers and the carboxyvinyl polymers sold under the trademark Carbopol.

Neutralizing agents, suitable for use in neutralizing acidic group containing hydrophilic gelling agents, include sodium hydroxide, potassium hydroxide, ammonium hydroxide, monoethanolamine, diethanolamine and triethanolamine.

Other optional materials include keratolytic agents such as salicylic acid; proteins and polypeptides and derivatives thereof; soluble or colloidally-soluble moisturizing agents such as hylaronic acid and starch-grafted sodium polyacrylates; coloring agents; perfumes and perfume solubilizers; surfactants/emulsifiers such as fatty alcohol ethoxylates and ethoxylated polyol fatty acid esters; and pigments which can be organic or inorganic and which include materials having a low color or lustre, such as matte finishing agents, and also light scattering agents.

The compositions of the present invention may be prepared by any conventional technique for preparing a cosmetic composition by merely substituting the agent in solution for the water normally incorporated into the composition.

Dental Applications

This invention also relates to a method of improving bone and periodontal regeneration. The method involves administering to the bone or periodontal area in need thereof an effective amount of a composition comprising at least one threitol phosphate selected from the group consisting of threitol monophosphate, threitol-bis-phosphate, threitol diphosphate, threitol triphosphate, and salts and derivatives thereof.

Administering the sSBD.4-containing composition to the bone or periodontal area may be accomplished through any means known in the dental field. For example, the composition may be administered orally, applied directly to the bone or periodontal area, by pump or injection, or via a slow-release matrix.

When administered to the bone or periodontal area, the composition preferably contains growth factor, an antibiotic, calcium, tricalcium phosphate, an excipient, collagen, hyaluronic acid, a suitable carrier, or combinations thereof.

The present invention having been described in detail in the preceding sections, the following examples are provided to illustrate certain aspects of, but not to limit, the invention.

EXAMPLES

Example 1

Preparation of Threitol-1-phosphates

To 2,3-O-Isopropylidene-D-Threitol (200 mg, 1.23 mmol) in pyridine (2 ml) was added DMTCl (418 mg, 1.23 mmol) at room temp. After 16 hrs, water and EtOAc (30 ml each) were added and the organic layer was separated and washed 4 times with water (30 ml) and brine. It was then dried over $MgSO_4$, filtered and concentrated to give 400 mg crude which was purified on silica gel to give 270 mg 2,3-O-Isopropylidene-D-Threitol 1-O DMT, the clean desired product (58%).

2,3-O-Isopropylidene-D-Threitol 1-O DMT (100 mg, 0.21 mmol) was then dissolved in dry pyridine (0.2 ml) and dry dioxane (0.6 ml) and reacted with 2-chloro-4H-1,3,2-benzodiozaphosphorin-4-one (0.21 mmol) in dry dioxane (0.2 ml). After 10 minutes tributylammonium pyrophosphate solution in dry DMF (0.5 M stock, 0.64 ml) and tributylamine (0.21 ml) were added and the reaction was allowed to stir for 15 min. $I_2$ solution in pyridine/water (98:2; 1% stock solution; 5.4 ml) was added to the reaction mixture. A 5% sodium sulfite solution (1.8 ml) was added after 10 minutes to quench excess iodine. Solvents were removed under high vacuum. The residue was dissolved in 50% acetic acid for 20 min at 0° C. followed by solvent removal. The residue was then dissolved in water (20 ml) and washed twice with diethyl ether. The aqueous layer was treated with sodium bicarbonate (1 g) to Ph=8 and washed with dichloromethane (3×30 ml) and ethyl acetate (20 ml). Then the aqueous layer was treated with washed Amberlite IR120, H⁺ form (8 g) for 30 min and filtered. The Ph of the filtrate was ~2, at which point it was concentrated under vacuum. The residue was triturated with methanol (5 ml), the white solid was separated and washed with methanol (3×5 ml) and dried under vacuum to give 9.5 mg of white solid. This results in a mixture of threitol-1-monophosphate, threitol-1-diphosphate, and threitol-1-triphosphate.

FIG. 1 depicts a synthesis scheme showing how this process can be used to prepare threitol tri, di, and monophosphate.

Example 2

Preparation of calcium salts of threitol-1-phosphates

To the threitol-1-phosphates prepared in Example 1, powder $Ca(OH)_2$ was added in water at a Ph of about 6 and concentrated under vacuum.

Example 3

Evaluation of threitol-1-phosphates

The threitol phosphates prepared in Example 1 were analyzed to determine their effectiveness in various tests.

Figure 2A:
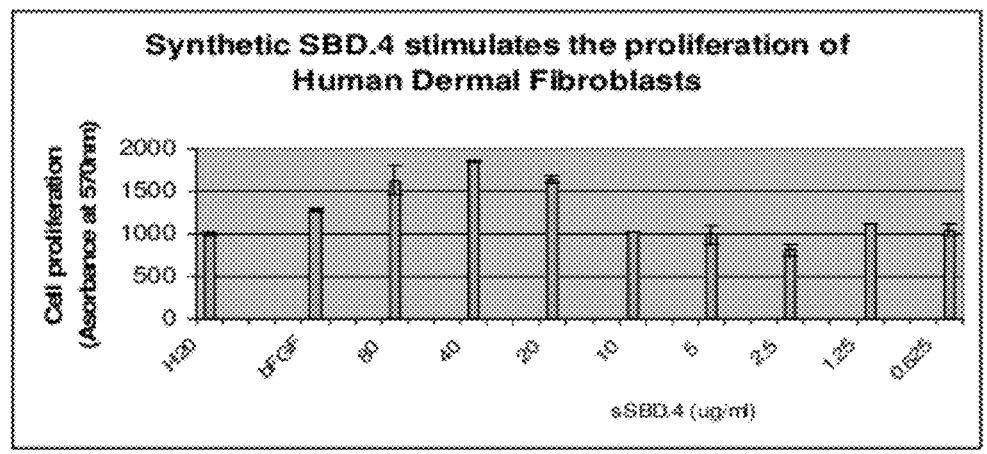

Example 3(a): FIG. 2 depicts the effect of sSBD.4 on the proliferation of human dermal fibroblasts (HDF) and on the type I collagen in the medium conditioned by these cells. In FIG. 2A, sSBD.4 at various concentrations is shown to stimulate the proliferation of HDF (human dermal fibroblasts), compared against water and bFGF (basic fibroblast growth factor). It is believed that the activity of the threitol phosphates is attributable mostly to the diphosphate, and possibly the triphosphate.

Figure 2B:
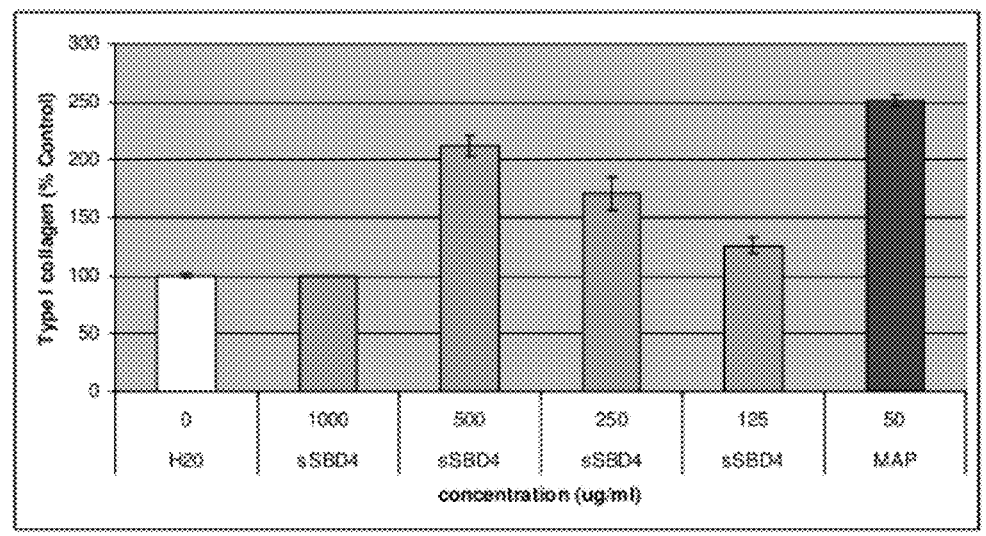

As can be seen in FIG. 2A, sSBD.4 stimulates the proliferation of human dermal fibroblasts. In FIG. 2B, sSBD.4 is shown to increase type I collagen levels in the HDF-conditioned medium, compared against MAP (magnesium ascorbyl phosphate). The results were measured by sandwich ELISA, according to Dobak et al. "1,25-Dihydroxyvitamin D3 increases collagen production in dermal fibroblasts" *J. Dermatol. Sci.* 8:18 (1994), herein incorporated by reference in its entirety. The results in FIGS. 2A and 2B show that treatment of human dermal fibroblasts with as much as 500 ug/ml and as little as 125 ug/ml of sSBD.4 results in the increase of type I collagen in the cell growth media. This collagen amount is more than doubled in the presence of 500 ug/ml of sSBD.4, as compared to water-treated control.

Figure 3:
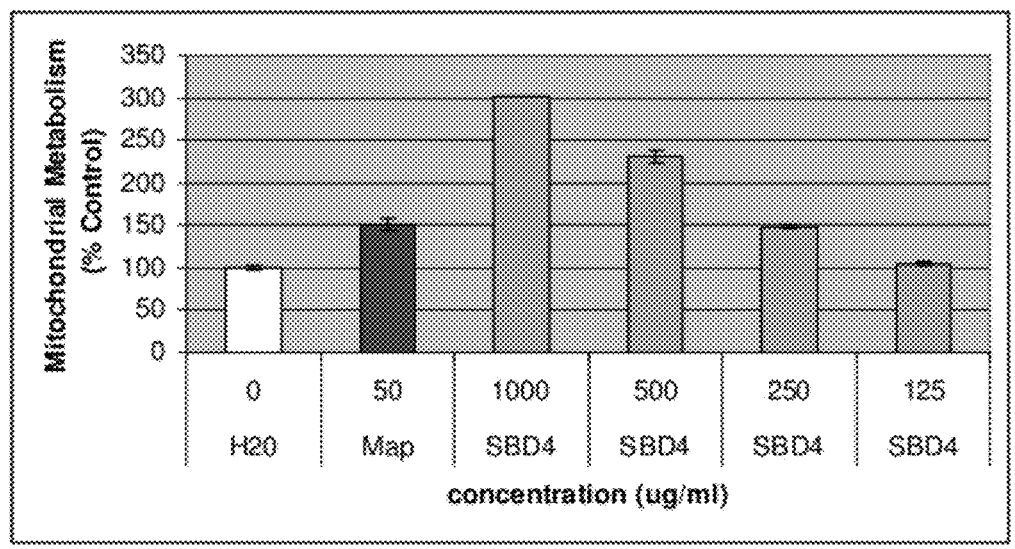
FIG. 3 shows a chart depicting the stimulatory effect of sSBD.4 on the mitochondrial metabolism in human dermal fibroblast populations as compared with magnesium ascorbyl phosphate (MAP).

Example 3(b): FIG. 3 depicts the stimulatory effect of sSBD.4 on the mitochondrial metabolism in human dermal fibroblast populations, compared against MAP. As can be seen in FIG. 3, sSBD.4 at 1000 ug/ml and 500 ug/ml outperforms 50 ug/ml MAP in stimulating the mitochondrial metabolism. This shows the utility of threitol phosphates for regenerative purposes of tissues containing fibroblasts.

Figure 4:
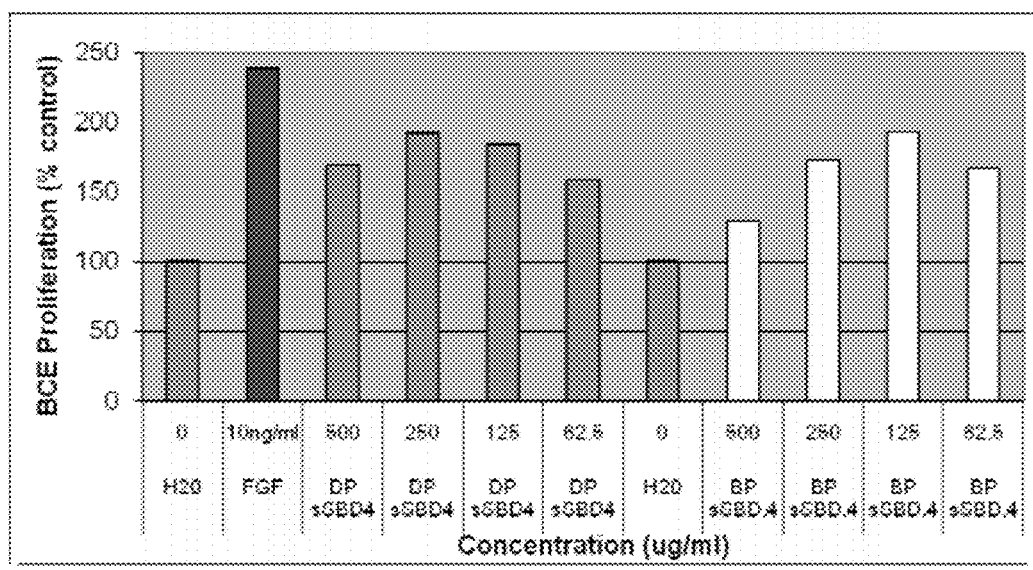
FIG. 4 shows a chart depicting the stimulatory effect of sSBD.4 on the proliferation of capillary endothelial cells as compared with basic fibroblast growth factor.

Example 3(c): FIG. 4 depicts the stimulatory effect of two types of sSBD.4 (threitol-1-diphosphate, labeled DP sSBD4, and threitol-1-bisphosphate, labeled BP sSBD4) on the proliferation of capillary endothelial cells (BCE), compared against basic fibroblast growth factor (FGF). As can be seen in FIG. 4, sSBD.4, in both its diphosphate and bisphosphate forms, stimulate the proliferation of capillary endothelial cells by over 90%. This shows the utility of sSBD.4 in the field of vascular regeneration.

Figure 5:
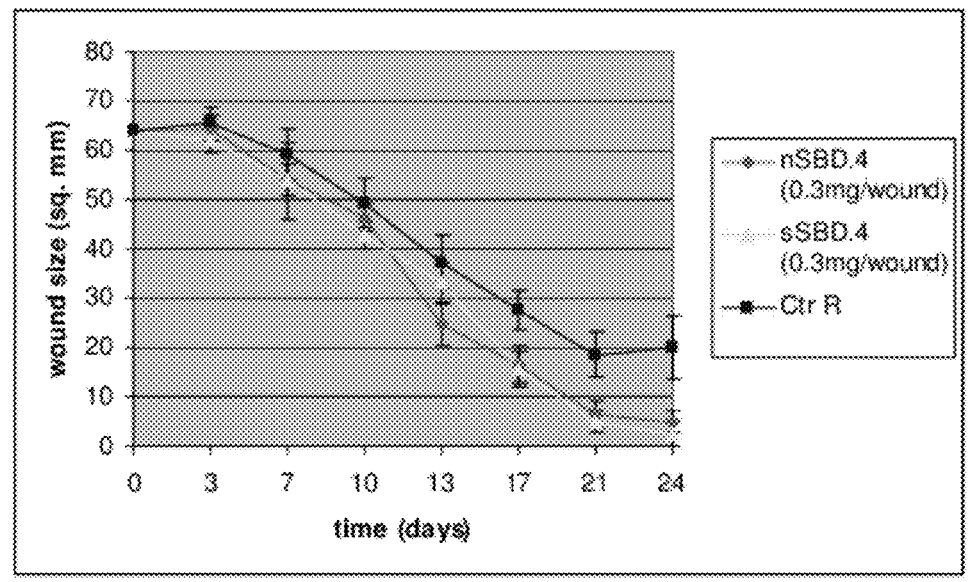
FIG. 5 shows a chart depicting the effect of threitol-1 diphosphate in 2% carboxymethylcellulose on cutaneous wound healing in genetically diabetic mice, compared against natural (plant-purified) SBD.4 in 2% carboxymethylcellulose, and a control vehicle (2% carboxymethylcellulose).

Example 3(d): FIG. 5 depicts the effect of sSBD.4 in 2% carboxymethylcellulose on cutaneous wound healing in the genetically diabetic mice, compared against natural (plant-purified) SBD.4 in 2% carboxymethylcellulose, and a control vehicle (2% carboxymethylcellulose). This example shows that the sSBD.4 stimulates cutaneous excisional wounds in diabetic mice as compared with control wounds.

Figure 6:
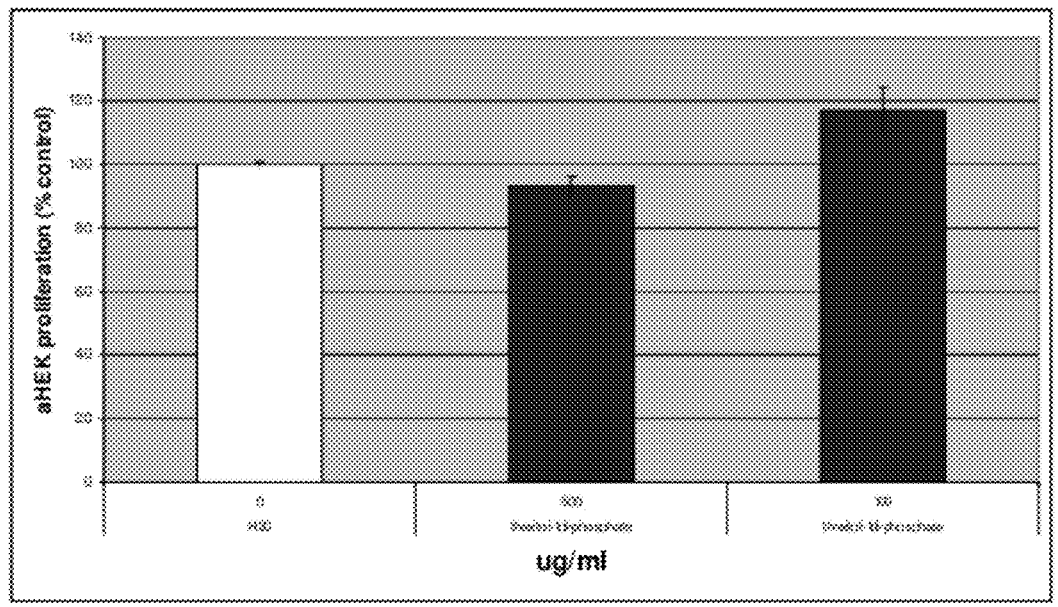
FIG. 6 shows a chart depicting effect of threitol-1 diphosphate on the proliferation of adult human epidermal keratinocytes (aHEK).

Example 3(e): FIG. 6 depicts the effect of threitol-1 diphosphate on the proliferation of adult human epidermal keratinocytes (aHEK). This graph shows that at 100 ug/ml threitol-1-diphosphate stimulates human adult epidermal keratinocyte proliferation by 17% (the comparative water example has a 0 µg/ml of test material).

We claim:

1. A composition comprising at least one purified threitol phosphate selected from the group consisting of threitol-monophosphate, threitol-bis-phosphate, threitol-diphosphate, threitol-triphosphate, their salts, and mixtures thereof, wherein the composition further comprises a UV-screening agent, a whitening agent, a skin-soothing agent or combinations thereof.

2. The composition of claim 1, wherein the threitol phosphate is in the salt form, and the salt is a calcium salt or a sodium salt.

3. The composition of claim 1, wherein the composition is a lotion, cream, gel, cleanser, shampoo, or conditioner.

4. The composition of claim 1, further comprising a pharmaceutically acceptable excipient.

* * * * *